United States Patent
Abbondanzio et al.

(10) Patent No.: US 7,641,364 B2
(45) Date of Patent: Jan. 5, 2010

(54) ADAPTER FOR LIGHT BULBS EQUIPPED WITH VOLATILE ACTIVE DISPENSER AND LIGHT EMITTING DIODES

(75) Inventors: Matthew Abbondanzio, Racine, WI (US); Mark E. Johnson, Mount Prospect, WI (US); Simon M. Conway, Burlington, WI (US); Kamran Faterioun, New Berlin, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 200 days.

(21) Appl. No.: 11/833,488

(22) Filed: Aug. 3, 2007

(65) Prior Publication Data
US 2008/0001551 A1   Jan. 3, 2008

Related U.S. Application Data

(63) Continuation-in-part of application No. 11/553,127, filed on Oct. 26, 2006, now Pat. No. 7,484,860, which is a continuation-in-part of application No. 11/426,055, filed on Jun. 23, 2006, now Pat. No. 7,318,659, which is a continuation-in-part of application No. 11/069,964, filed on Mar. 3, 2005, now Pat. No. 7,246,919, said application No. 11/426,055 is a continuation-in-part of application No. 10/561,822, filed on Apr. 25, 2006.

(60) Provisional application No. 60/549,154, filed on Mar. 3, 2004, provisional application No. 60/483,913, filed on Jul. 2, 2003.

(51) Int. Cl.
F21V 23/00 (2006.01)
(52) U.S. Cl. .................. 362/295; 362/253; 362/643; 362/650

(58) Field of Classification Search ................. 362/295, 362/253, 643, 650
See application file for complete search history.

(56) References Cited

U.S. PATENT DOCUMENTS

| 4,694,215 A | 9/1987 | Hofmann |
| 5,286,216 A | 2/1994 | Volz |
| 5,531,616 A | 7/1996 | Forestello |

(Continued)

FOREIGN PATENT DOCUMENTS

WO   2005029652 A   3/2005

OTHER PUBLICATIONS

PCT/US2008/009339 International Search Report and Written Opinion dated Dec. 2, 2008.

*Primary Examiner*—Sandra L O'Shea
*Assistant Examiner*—Evan Dzierzynski

(57) ABSTRACT

An adapter device for a lamp or light fixture includes a male connector, a female socket and control circuitry. The adapter supports at least one RGB LED cluster positioned so as to emit a colored light show. The male connector is configured to be received in a conventional light socket. The adapter also includes a slot for receiving and securing a replaceable volatile active insert for enabling the device to emit an active ingredient from the insert when the insert is secured in the slot. A conventional light bulb or a CFL may also be connected to the female socket as a source of illumination. Thus, a single adapter is used to combine a conventional light source/colored light show source/volatile active source.

21 Claims, 10 Drawing Sheets

U.S. PATENT DOCUMENTS

| | | |
|---|---|---|
| 5,534,840 A | 7/1996 | Cuingnet |
| 5,655,830 A | 8/1997 | Ruskouski |
| 5,700,154 A | 12/1997 | Geary |
| 5,759,054 A | 6/1998 | Spadafore |
| 5,952,792 A | 9/1999 | Borowiec et al. |
| 6,218,785 B1 | 4/2001 | Incerti |
| 6,478,440 B1 * | 11/2002 | Jaworski et al. ............... 362/96 |
| 6,685,479 B1 * | 2/2004 | Ghaly ........................ 434/236 |
| 6,686,681 B1 | 2/2004 | Allgeier et al. |
| 6,688,753 B2 * | 2/2004 | Calon et al. ................. 362/236 |
| 6,779,905 B1 * | 8/2004 | Mazursky et al. ........... 362/101 |
| 6,910,791 B2 * | 6/2005 | Futami ....................... 362/517 |
| 6,965,205 B2 | 11/2005 | Piepgras et al. |
| 7,083,162 B2 * | 8/2006 | He et al. .................... 261/142 |
| 7,109,665 B2 | 9/2006 | Green |
| 7,161,311 B2 | 1/2007 | Mueller et al. |
| 7,161,313 B2 | 1/2007 | Piepgras et al. |
| 7,221,105 B2 | 5/2007 | Chliwnyj et al. |
| 7,224,125 B2 | 5/2007 | Ribarich |
| 7,227,634 B2 | 6/2007 | Cunningham |
| 7,228,190 B2 | 6/2007 | Dowling et al. |
| 2004/0109317 A1 | 6/2004 | Ribarich |
| 2005/0185392 A1 | 8/2005 | Walter et al. |
| 2005/0238222 A1 * | 10/2005 | Nakano et al. .............. 382/151 |
| 2006/0045818 A1 | 3/2006 | Moreland |
| 2006/0092641 A1 | 5/2006 | Phelan et al. |
| 2006/0119287 A1 | 6/2006 | Campbell et al. |
| 2006/0125420 A1 | 6/2006 | Boone et al. |
| 2006/0146527 A1 * | 7/2006 | VanderSchuit .............. 362/228 |
| 2006/0152161 A1 | 7/2006 | Rodriguez |
| 2006/0221593 A1 | 10/2006 | Alden |
| 2006/0237439 A1 | 10/2006 | Norwood et al. |
| 2006/0238163 A1 | 10/2006 | Chen |
| 2006/0263733 A1 | 11/2006 | Furner et al. |
| 2007/0014549 A1 | 1/2007 | Demarest et al. |
| 2007/0020572 A1 | 1/2007 | Furner et al. |
| 2007/0020573 A1 | 1/2007 | Furner et al. |
| 2007/0086199 A1 | 4/2007 | Demarest et al. |
| 2007/0248502 A1 * | 10/2007 | Adair et al. ................. 422/120 |

* cited by examiner

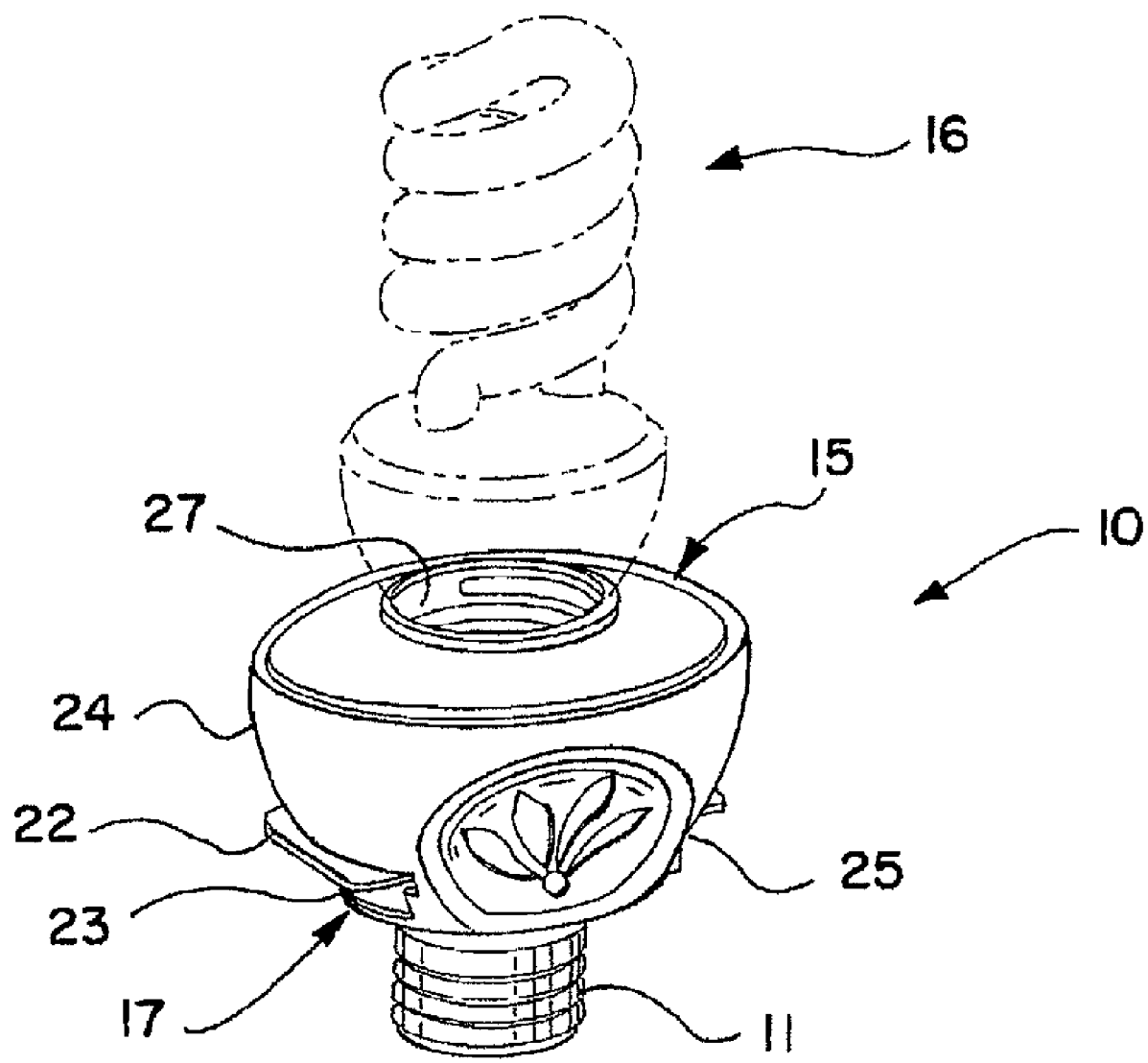
FIG. IA

FIG. 7B

| BUTTON SEQUENCE/ACTION | RESULT |
|---|---|
| 1 PRESS | INITIAL STATE - POWER ON<br>CFL ON<br>LEDS OFF |
| 2 PRESSES | EXECUTE LIGHT SHOW #1 |
| 3 PRESSES | EXECUTE LIGHT SHOW #2 |
| 4 PRESSES | EXECUTE LIGHT SHOW #3 |
| 5 PRESSES | EXECUTE LIGHT SHOW #1<br>EXECUTE LIGHT SHOW #2<br>EXECUTE LIGHT SHOW #3<br>RETURN TO #1 AND REPEAT PATTERN |
| 6 PRESSES | ALL OFF |
| 7 PRESSES | RETURN TO INITIAL STATE |
| INTERRUPT ACTION | RESULT |
| PRESSING AND HOLDING FOR 2 SECONDS DURING ANY LIGHT SHOWS | LEDS BLINK FOR 1 SECOND AND LIGHT SHOW FREEZES |
| PRESS AGAIN | RETURN AND BEGIN NEXT SEQUENCE |

26

ADAPTER FOR LIGHT BULBS EQUIPPED WITH VOLATILE ACTIVE DISPENSER AND LIGHT EMITTING DIODES

CROSS-REFERENCE TO RELATED APPLICATIONS

This application is a continuation-in-part of U.S. patent application Ser. No. 11/553,127, filed Oct. 26, 2006, which is a continuation-in-part of U.S. patent application Ser. No. 11/426,055, filed on Jun. 23, 2006, still pending, which is a continuation-in-part of U.S. patent application Ser. No. 11/069,964, filed on Mar. 3, 2005, still pending, which claims priority to Provisional Patent Application Ser. No. 60/549,154, filed on Mar. 3, 2004. Said application Ser. No. 11/426,055 is also a continuation-in-part of U.S. patent application Ser. No. 10/561,822, filed on Jul. 2, 2004, still pending, which claims priority to Provisional Patent Application Ser. No. 60/483,913 filed on Jul. 2, 2003.

BACKGROUND

1. Technical Field

An adapter for a conventional light bulb is disclosed that includes a plurality of colored light emitting diodes (LEDs) and a volatile active dispenser. Circuitry in the adapter enables various combinations of volatile active emission, illuminating light emission, colored light shows and low level white or colored light emission.

2. Description of the Related Art

Creating a pleasant ambience is a popular aspect of home decor. This is often achieved through various combinations of pleasant fragrances and mood lighting. Lighting can also be combined with other functions such as air sanitization, air deodorization, and the controlled release of insect repellent, insect attractant and insecticide. Conventional products such as scented candles, mood lighting devices, fragrance dispensers, and the like, are commonly used to create a pleasant environment in the home. While those conventional products help to create a pleasant living environment and ambiance, they have their drawbacks.

For example, while scented candles create soft light and fragrance, which creates a pleasant mood, candles are a potential fire hazard and often produce unwanted smoke and wax drippings. Traditional light fixtures and lamps do not provide the color effects, fragrance emission or other active emission that users often desire. While stand-alone aesthetic devices are available for providing lighting effects (such as color changing and the like), these standalone devices take up space around the home and add to the clutter that many consumers are trying to avoid. Also, because such stand-alone devices are typically placed in highly visible locations, they need to be aesthetically designed to suit the personal tastes of different categories of buyers, requiring additional design costs.

Conventional fragrance dispensers, such as plug-in diffusers, can provide pleasing aromas in a relatively inexpensive, compact package. However, such conventional fragrance dispensers generally take up outlets and are often located out of sight, causing a user to forget to adjust or refill the device. While these fragrance dispensers may also provide light, because the devices are used in existing electrical outlets, they are generally positioned too low to provide effective lighting features, other than to operate as a nightlight.

Conventional nightlights include only white light emission in combination with fragrance emission. While a single scent may be provided in the form of a decorative diffuser, colored nightlights are not generally available and there is no coordination between the light color emitted and the particular fragrance emitted. Further, sophisticated multi-colored lights that change color and that are aesthetically pleasing in combination with fragrance emission are not currently available.

Further, numerous needs exist for providing the combination of white light and/or colored light with volatile active emissions other than fragrances, such as air sanitization, air deodorization, the controlled release of insect repellent, insect attractant, insecticide, aromatherapy volatiles or other non-fragrant materials (any of which may be combined with fragrant materials if necessary to make the ambient environment more tolerable).

Therefore, multiple needs exist for devices that provide for the combination of one or more of the following functions: white light emission; colored light emission; colored light shows; fragrance emission; air sanitization; air deodorization; insecticide emission; insect repellent emission; aromatherapy material emission; light emission that repels insects; light emission that attracts insects; and any combinations thereof.

SUMMARY OF THE DISCLOSURE

In view of the drawbacks of the lighting and fragrance devices currently on the market, adapter devices are disclosed herein which provide various combinations of lighting and emission of volatile actives.

An adapter for receiving an illuminating light source such as a conventional light bulb, a coiled fluorescent lamp (CFL) or a white LED is disclosed which provides for various combinations of features including, but not limited to, the emission of illuminating light, colored light in the form of changing colored light shows and volatile active ingredient emission. The disclosed device screws into a conventional socket and the active ingredient is dispensed from replaceable cartridges or inserts removably received within a slot disposed on the adapter. The device circuitry provides colored light shows, power to the illuminating light, and an optional heating circuit for increasing the emission or output rate of the active ingredients. The specific active ingredient emitted may be coordinated with the specific colored light show performed. A plurality of colored light shows may be programmed into the memory of the device and memory chips containing new colored light shows may be provided or the active ingredient inserts may be equipped with a chip containing one or more colored light shows that are designed with the active ingredient in mind. The colored light may be produced by red, green and blue (RGB) light-emitting diode (LED) clusters. The LEDs may also be used to emit low level white light or act as a "night light."

The adapter device intended primarily for use indoors combines one or more of the following: white light emission with optional white light intensity adjustment or dimming; selectable colored light shows; low level night light illumination; and fragrance and/or volatile active emission without adding clutter to a room, without requiring the purchase of new fixtures, without taking up additional electrical outlets, without requiring aesthetically pleasing designs for the unit itself, and without presenting the fire hazards associated with open flames. Alternatively, the adapter could be used in outdoor lighting schemes.

In such a refinement, an adapter for a conventional light bulb that can be used indoors or outdoors is disclosed that is configured to mate with a conventional, Edison-type, light socket. The adapter includes a base with a male end received in a conventional light socket and a female receptacle that receives an illuminating light source (e.g., incandescent light, CFL, white LED, halogen bulb, etc.). The base also includes at least one RGB LED cluster positioned within the base so as to emit white light, colored light, and colored light shows. And the base includes a replaceable active ingredient cartridge or insert that may be received in a compartment or slot disposed on the base. Thus, the adapter can provide various combinations of functions such as various levels of white light, aesthetically pleasing colored lighting effects, fragrance emission and/or some sort of volatile active ingredient emission (e.g., insect repellent, insecticide, air sanitizer, air deodorizer, etc.).

In another aspect, a disclosed device includes a base configured to mate with a light socket for receiving the light bulb, a female receptacle for receiving an illumination light source, a translucent diffuser coupled to the base at least one RGB LED cluster. An active ingredient dispenser is supported by the base and dispenses an active ingredient from the device when the active ingredient is provided therein. A control mechanism is provided, by which the device can be controlled by a user to change at least one of the color of the light or colored light show emitted through the diffuser by LEDs, and an output rate of the active ingredient.

In a refinement, intensity adjustment or dimming of the white light source as well as the colored light effects or colored light shows can be provided.

As noted above, the disclosed device may receive a white light typically associated with a conventional light bulb, CFL or white LED, and provide colored options, color-changing effects, and/or active emission such as fragrance emission. In addition, all of these options may be provided in one device that can be placed in existing lamps already found in the user's home. Heat for enhancing the active emission can be supplied by a white light source, colored light source or heater built into the device and controlled by the circuitry of the device.

In a refinement, the volatile active ingredient controls, attracts, repels and/or terminates insects. The insect control functions may be combined with fragrance emission, a deodorizing function or an air sanitization function.

Thus, in a refinement, the volatile active may provide a function selected from the group consisting of: insect control, insect termination, insect attraction, insect repellency, moth termination, fragrance emission, or deodorization, air sanitization, aromatherapy, volatile medicine emission and any combination thereof.

In a related refinement, a device made in accordance with this disclosure can release an active that repels insects, such as mosquitoes, to either keep such insects out of a home or to keep such insects away from an outdoor area such as a patio or porch. The active can repel or kill the problematic insects. In the alternative, the disclosed devices may be used to attract insects and keep them away from an outdoor area such as a porch or deck. Indoor applications include the use of a disclosed device in a closet that emits a volatile active that kills moths and further that emits white light or, optionally, colored light. The disclosed devices may also be used to emit insect repellent or insecticides indoors in certain jurisdictions and therefore these functions can be combined with the emission of white light and/or colored light shows.

Thus, the combination white light/colored light show/active emitter device disclosed herein can be used in porch/deck lighting systems and outdoor perimeter lighting systems.

In another refinement, combination white light/colored light show/active emitter device can be used in an enclosed area such as a closet and the volatile active can be an insecticide directed at moths, roaches, houseflies, fruit flies, gnats and/or ants.

In a refinement, the LEDs may be used to provide an additional or an alternative source of white light.

In a refinement, light sources, either white or colored, may be used as heat sources for active ingredient emission.

In another refinement, the fragrance or active delivery may be provided by scented oil or scented gels provided in cartridges or inserts which may be replaceably secured in/to the device, to provide the desired fragrance emission. This allows a user to change between different fragrances and/or replace empty inserts, without the need to change the entire adapter or base device. In addition, the device can be programmable so that a user may change the lighting options (e.g., change the brightness or color, activate a color show or change color shows), and/or the fragrance emission rate.

In another refinement, the refill cartridge or insert includes a memory chip programmed with one or more colored light shows and in a further refinement of this concept, the colored light shows are coordinated with the active contained in the refill insert. In short, either the fragrance emitted or another type of active, such as insect repellant, can be coordinated with the one or more colored light show exhibited by the device. Alternatively, a switch means on an insert may automatically select a particular light show from the memory when inserted into the device.

In another refinement, a refill cue may be provided by the circuitry of the device that informs the user when the active or fragrance has become depleted and when a refill cartridge or insert is needed.

In another refinement, a remote control device may be provided enabling the user to change colored light shows, stop a colored light show and turn the light source on or off. The remote control device may also be provided with a fragrance or active dispenser.

In another refinement, one or more control buttons or switches may be provided on the outside of the base or base housing which enables the user to change colored light shows, stop or pause a colored light show, turn the fluorescent lamp on or off, or turn the device on or off.

Other advantages and features will be apparent from the following detailed description when read in conjunction with the attached drawings.

BRIEF DESCRIPTION OF THE DRAWINGS

For a more complete understanding of the disclosed methods and apparatuses, reference should be made to the embodiment illustrated in greater detail on the accompanying drawings, wherein:

FIG. 1A is an elevational view of a disclosed adapter that has received a CFL, although it will be noted that other threaded light bulbs or illuminating light sources may be employed, and wherein the adapter includes a volatile active dispenser.

FIG. 7B is a table of an exemplary program corresponding to subsequent button or switch presses and actions for the adapters shown herein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION OF THE PRESENTLY PREFERRED EMBODIMENTS

Figure 1B:
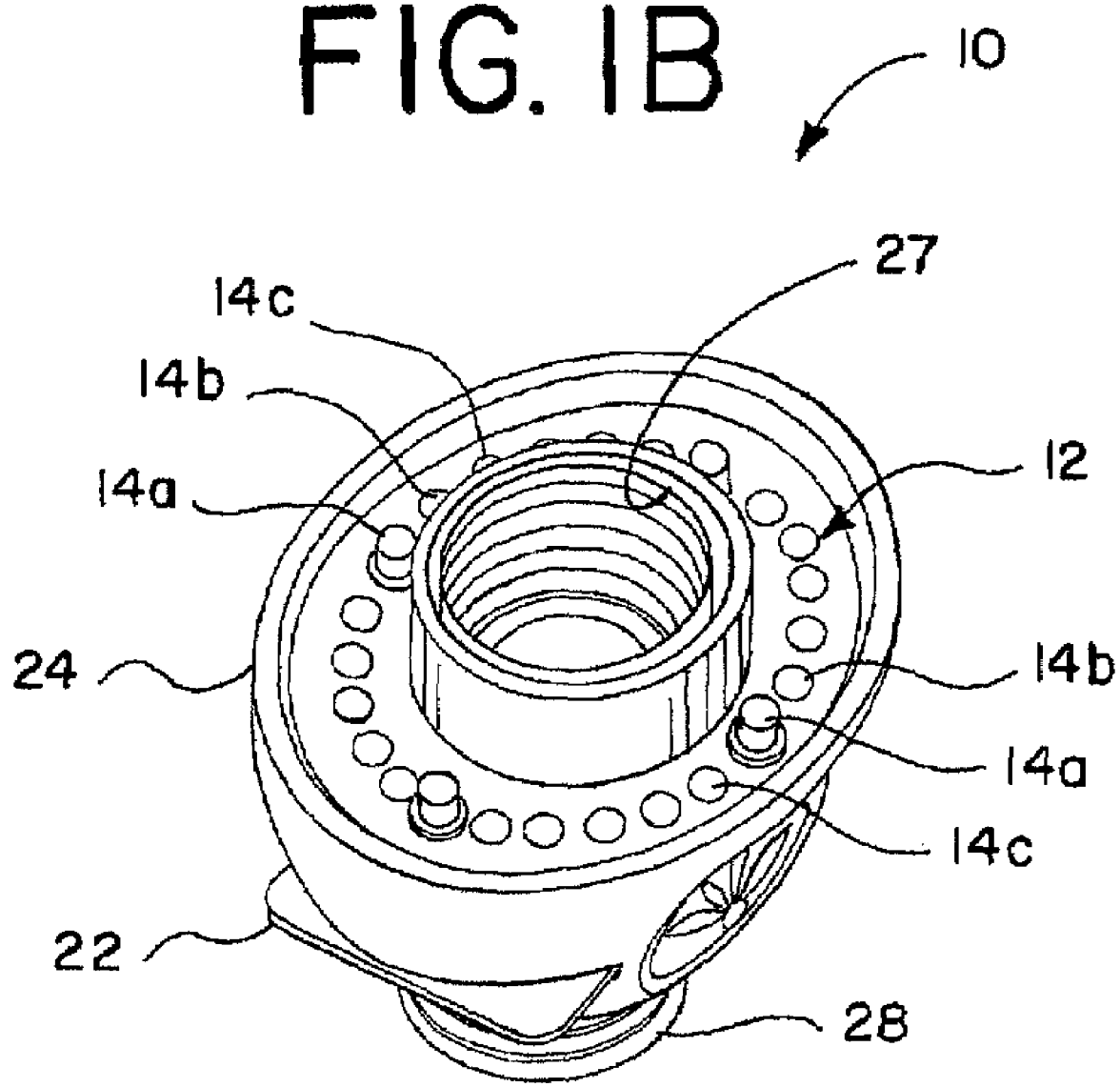
FIG. 1B is an elevational view of the adapter of FIG. 1A shown without a bulb or top cover.
Figure 2A:
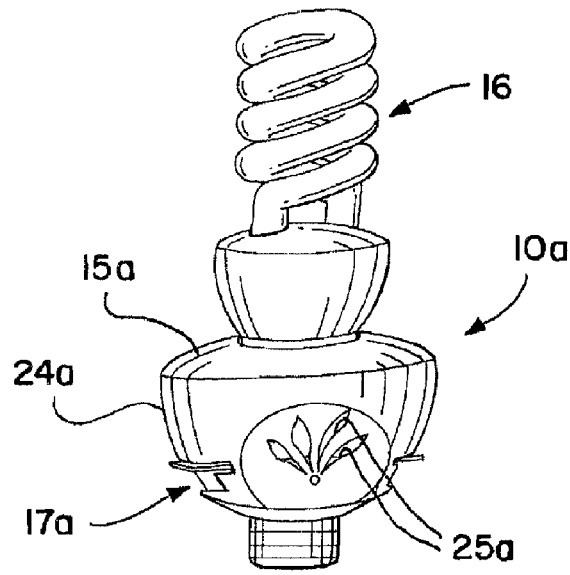
FIGS. 2A-2D are perspective, front, left side and right side views of another adapter that has currently received a CFL, wherein the adapter includes a volatile active dispenser.
Figure 2B:
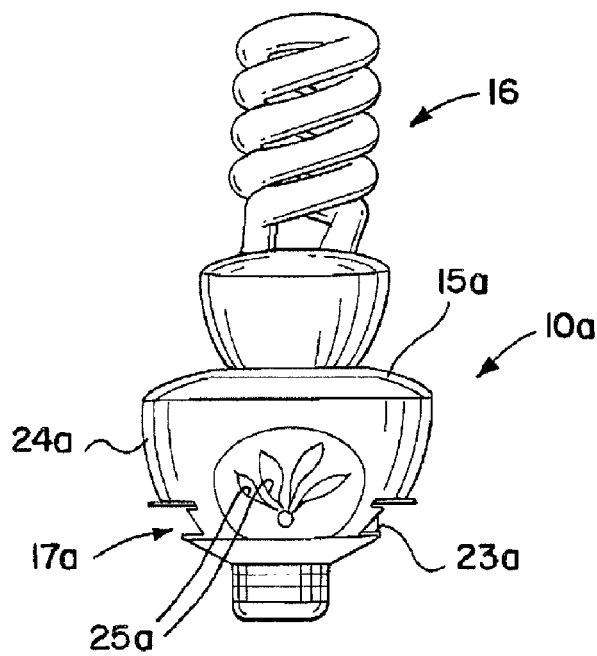
Figure 2C:
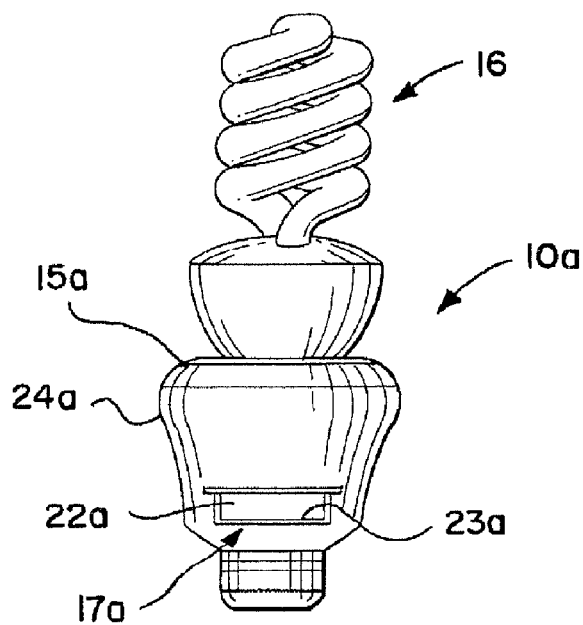
Figure 2D:
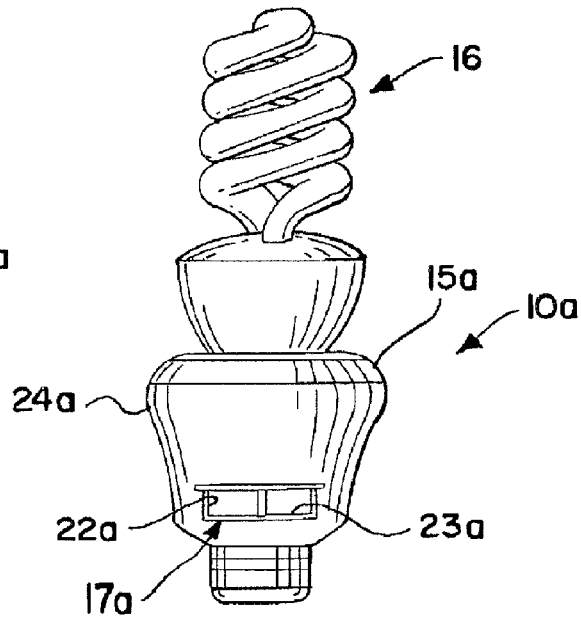

FIGS. 1A-1B illustrate a screw-in combination light source and controlled volatile active dispenser adapter device 10 made in accordance with this disclosure. While the disclosed device 10 may mate with any one of a number of lighting fixtures (such as conventional fixtures for receiving incandescent, halogen, or fluorescent bulbs), for exemplary purposes, the description provided herein refers to an Edison-type, screw-in adapter 10 that mates with a conventional incandescent light socket with a threaded female socket. Of course, the devices disclosed may be embodied with any light bulb that mates with a light socket and/or power source.

The adapter 10 of FIGS. 1A-1B comprises a threaded male connector 11a, which is configured to mate with a threaded female socket of a conventional lamp or other lighting fixture. When connector 11a is mated with such a socket, AC power is provided to the device 10 from the lamp or lighting fixture.

The power is provided to an LED board light array 12, on which LEDs 14 are mounted. The LEDs 14 can be provided in a three-diode cluster including red 14a, green 14b and blue 14c diodes referred to below as a RGB LED cluster. These LEDs 14 may be operated in any one of a number of combinations to provide a specific color of light, color shows or patterns that are pleasing to a user. For example, the LEDs 14 may be operated as described in commonly assigned International Publication No. WO2005/003625, U.S. Publication Nos. U.S. 2005/0169812 and U.S. 2005/0169666, all of which are incorporated herein by reference. A diffuser 15 may be provided on the adapter 10. Such a diffuser 15 operates to combine the lights from the different LEDs 14 to form a single color, the perception of which is dictated by the relative intensities of the individual colored LEDs 14. In other embodiments, no diffuser 15 at all may be used, in order to allow a user to simultaneously perceive multiple colors of the different LEDs 14. Also, when insect control is an issue, the lighting effects may be programmed to attract or repel insects, using conventionally known lighting techniques for the same.

Still referring to FIGS. 1A-1B, the LEDs 14 can provide a primary illumination source for the adapter 10 but the more preferable method is to employ a fluorescent lamp as a white light source and, more specifically, the twisted or coiled fluorescent lamp (CFL) 16 as shown in FIGS. 1A and 2A-2D. The red 14a, green 14b, and blue 14c LEDs may be configured to, in combination, produce white light, when their respective wavelengths are mixed by the above-referenced diffuser 15 or the like. See also FIG. 3 below. Other conventional light sources, such as halogen, white LED or other types of fluorescent lights may also be used as a primary light source. In the embodiments shown in FIGS. 1A and 2A-2D, a CFL 16 is coupled to the adapter 10, and provides the primary source of illumination. Alternatively, when the CFL 16 is used, the RGB LED cluster may be omitted and vice versa.

Figure 4:
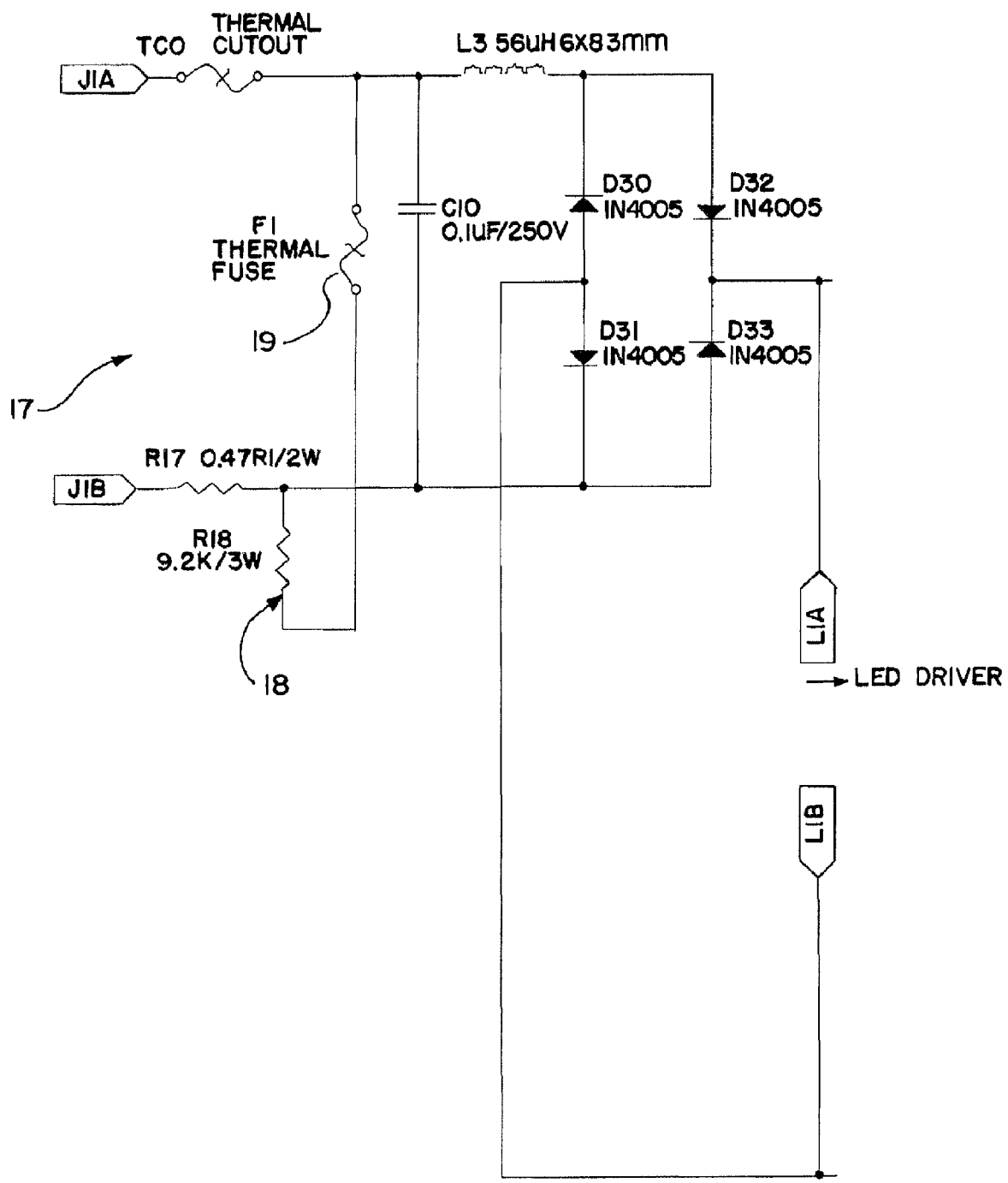
FIG. 4 is a circuit diagram of a rectifier and an exemplary heater circuit for the adapters shown herein.

Power is also preferably provided to volatile active dispenser 17, which, in the exemplary circuit diagram of FIG. 4, may comprise a resistance heater 18 and thermal fuse F1. The heater resistor 18 is provided in the form of a metal oxide resistor or wire wound resistor potted in a ceramic block. Of course, other heating devices may be used for the heater 18, such as a Positive Temperature Coefficient (PTC) heater, a coil resistance heater, printed circuitry, an etched foil heating device, or the like. When in use, heater 18 generates heat for heating the active ingredient of liquid or gel formulations stored in a replaceable volatile active insert 22 that is received in the slot 23 disposed in the base or base housing 24. Vents 25 are provided to facilitate the release of the active. Such arrangements of heat-assisted evaporation devices are known in the art, and will not be described in detail herein. In general, however, insert 22 contains a formulation/active ingredient whose evaporation rate increases with the application of heat, thus allowing the evaporation rate (and consequently, the potency) to be controlled as the heat is varied.

Heat is applied to increase the evaporation rate of fragrance oil, fragrance gel, insecticide, insect repellent, insect attractant, air sanitizer, deodorizer, medicine, aromatherapy material or the like. In other embodiments, fan-assisted evaporation devices, piezo-electrically actuated atomization devices, and/or unassisted fragrance dispensers may be substituted for the resistance heater 18. Unassisted volatile active dispensers may simply include venting mechanisms that expose the volatile active to the ambient environment, or other such designs that enhance/provide convective airflow across a volatile active delivery medium. Of course, if unassisted volatile active dispensers are used, power need not be provided to the dispenser. These alternative devices are known in the art, and will not be described in detail herein.

Regarding the use of insect control actives, the disclosed devices may be particularly useful for patio/deck lighting and outdoor promoter lighting where it is desirable to keep insects away from a defined area such as a patio, deck or pool area and/or to attract insects away from such a defined area. Still further, use of the disclosed devices in an enclosed area such as the closet provides the opportunity for the volatile active to be a moth, cockroach, housefly, fruit fly, ant, gnat or other household insect killer or repellent.

Therefore, an ingredient suitable for inclusion in the volatile active cartridges or inserts 22 disclosed herein, or passive dispensers disclosed herein, is a fragrance, air freshener, deodorizer, odor eliminator, malodor counteractant, insecticide, insect repellant, medicinal substance, aromatherapy substance, disinfectant, sanitizer, mood enhancer, or the like, in liquid, oil or gel form, although gels and oils are preferred.

Preferably, if a fragrance is to be dispensed, the fragrance or air freshener is a fragrance comprising one or more volatile organic compounds which are available from perfumery suppliers such as Firmenich Inc., Takasago Inc., Noville Inc., Quest Co., International Flavors & Fragrances, and Givaudan-Roure Corp. Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components. Synthetic types of fragrance compositions either alone or in combination with natural oils are described in U.S. Pat. Nos. 4,324,915, 4,411,829, and 4,434,306, which are incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

A liquid fragrance may also be formed into a thixotropic gel by the addition of a thickening agent, such as a cellulosic material, a polymeric thickener, or a fumed silica of the type marketed under the Cabosil trademark by Cabot Corporation. A fragrance ingredient can also be in the form of a crystalline solid, which has the ability to sublime into the vapor phase at ambient temperatures. A crystalline fragrance starting material can be selected from organic compounds which include vanillin, ethyl vanillin, coumarin, tonalid, calone, heliotropene, musk xylol, cedrol, musk ketone benzophenone, raspberry ketone, methyl naphthyl ketone beta, phenyl ethyl salicylate, veltol, maltol, maple lactone, proeugenol acetate, evemyl, and the like. This type of fragrance can contribute a long term air-treatment capability to an air freshener dispenser device for use with the devices disclosed herein.

Suitable insect repellents, insect attractants and insecticides are well-known and will be apparent to those skilled in the art.

In addition to the compartment or slot 23 shown in FIGS. 1A-1B and 2A-2D, any one of a number of known mounting mechanisms may be used to removably secure the insert 22 in the slot 23, but preferably, the insert 22 slides into slot 23, so as to become wedged therein, or snaps into place using a system of mating protrusions and recesses. This allows the user to easily remove and replace spent inserts 22 or the like that serve as reservoirs for containing fragrance oils, with the oils being communicated from the reservoir to the ambient environment with or without a porous wick, or gel inserts which, when mounted, expose a gel impregnated with fragrance to the ambient environment.

Figure 5:
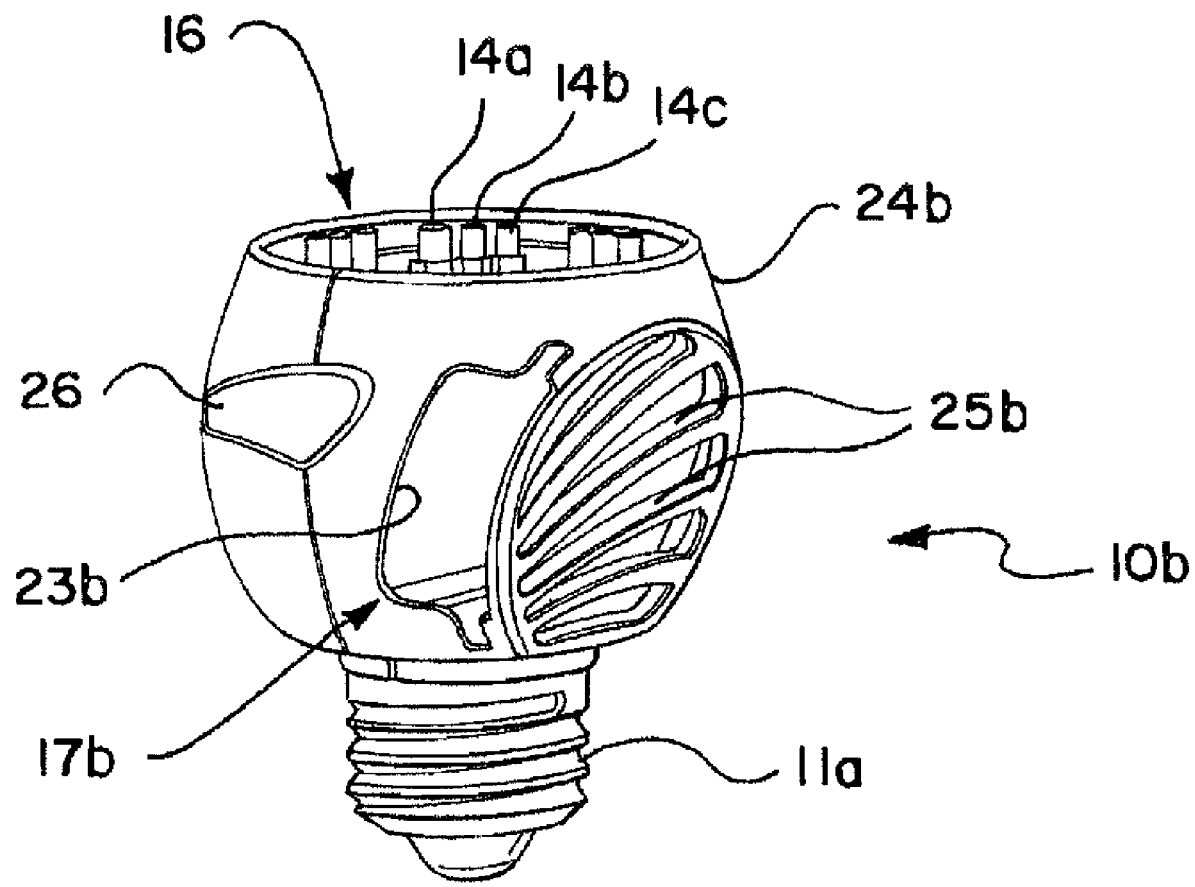
FIG. 5 is a perspective, left side view of another adapter having a control switch, RGB clusters and a slot for a replaceable insert.

A control switch 26 is provided on the adapter 10, as shown in another exemplary embodiment of FIG. 5, to allow a user to control the operations of the adapter 10. Although a switch 26 is shown herein for exemplary purposes, any one of a number of user interfaces may be used so that the user may adjust the setting of the adapter 10 such as interfaces including one, two, three or more buttons. A lanyard-type switch may also be employed. Such adjustments made include using a switch 26 or an interface to change the color of the light emitted from the RGB LED clusters, adjusting the brightness of the LEDs 14, switching between white light, colored light, and off settings, scrolling through the various colored light shows available in the memory of the device, adjusting the evaporation rate of the fragrance (e.g., by adjusting the heat level, when a heat assisted device is used), and/or setting predetermined programs for colored light shows or fragrance emission changes that may be stored in a memory and operated by a processor (as discussed in more detail below). In preferred embodiments, the user interface is a button or switch 26 that may be toggled to change the operation of the adapter 10 between different predetermined settings. For example, some suitable user interfaces are described in commonly assigned U.S. application Ser. Nos. 10/561,822 and 11/327,167, which are also incorporated herein by reference.

Each of FIGS. 1A-1B, 2A-2D and 5 discloses adapters 10, 10a and 10b that may or may not be provided with a white light source that, in this case, is a CFL 16. Thus, the white light source may be sold separately. However, it will be noted that the threaded female receptacle or socket 27b is capable of receiving other types of lights, such as incandescent lights and may be a plug connection, rather than a threaded connection.

Figure 6:
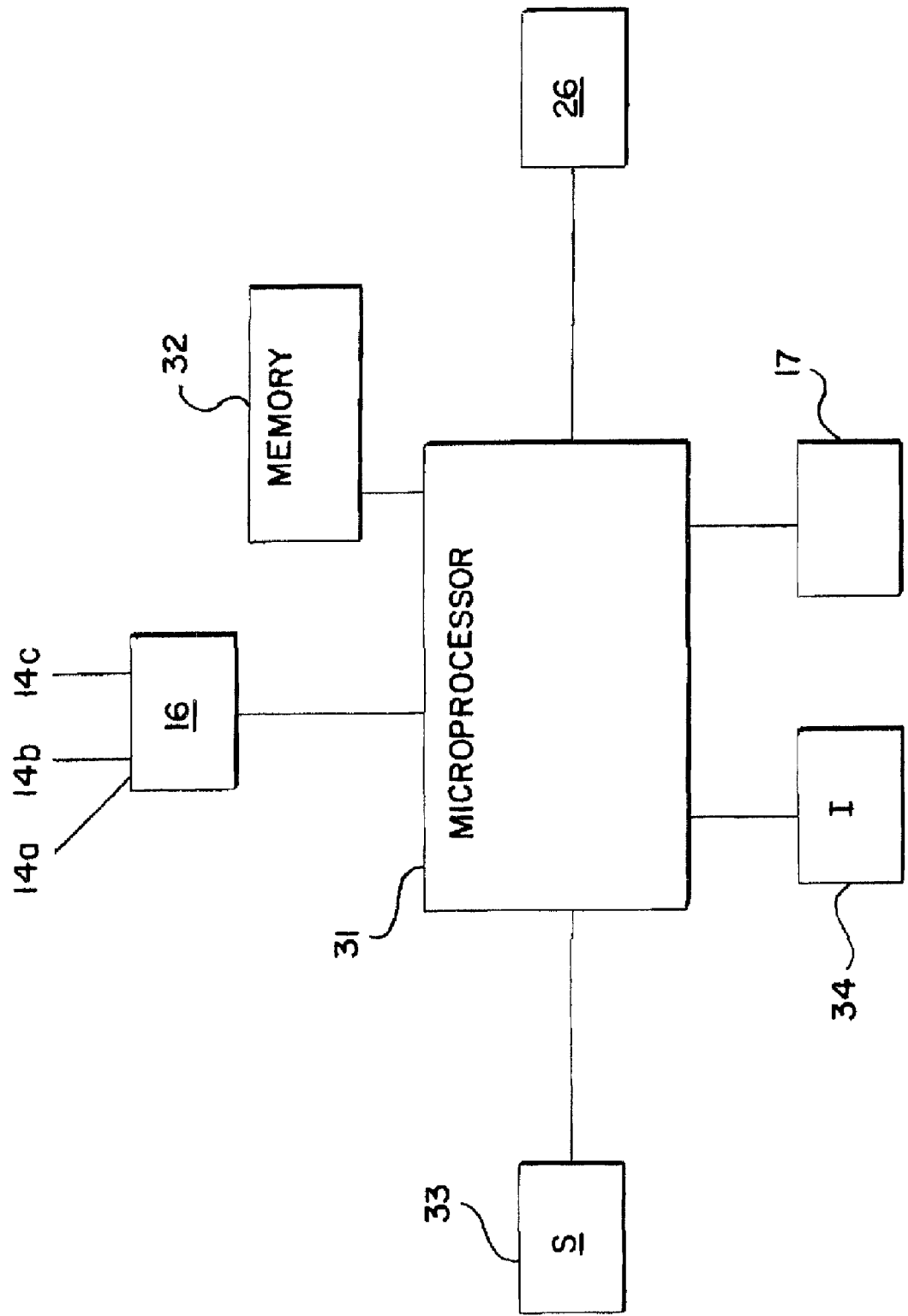
FIG. 6 is a schematic diagram of functional units of the combination light/colored light show/volatile active emission adapters disclosed herein.

FIG. 6 shows a diagrammatic representation of functional units of the adapter 10 of FIGS. 1A-1B and 2A-2D. Microprocessor 31 is a programmable controller that produces output signals to control the emission of light from the LEDs 14 of light array 16, and the amount of active emitted from the dispenser 17. Alternatively, one or more of the control features may be mechanically set by a user, without the assistance of a microprocessor. Such basic controls would be readily understood by one of ordinary skill in the art. Preferably, however, microprocessor 31 produces and outputs the signals to operate these devices according to one or more programs stored in the memory 32. The programs may be preset in the memory 32 and then selected and activated by a user through a user interface (e.g., switch 26). Additional colored light shows may be provided in the form of a supplemental memory chip associated with a replacement insert 22, or a memory chip that is received within a slot 23 disposed in the base housing 24 or the adapter 10. The signals may be in the form of voltages, coded pulses, or other signals, which control the operation of the components. Alternatively, the control switch 26 may set the lighting condition without reference to a stored program.

Operation of microprocessor 31 may also be activated to produce a presentation according to a signal from a sensor 33. Sensor 33 may include, for example, a motion sensor, a sound sensor, a timing sensor, an infrared sensor, a power source-monitoring sensor, or the like. If a power source-monitoring sensor is used, the microprocessor 31 may be configured to activate and/or change the presentation of light and/or fragrance when a power switch of a light socket or lamp in which the bulb is received is toggled (e.g., one toggle activates the fluorescent light source, two toggles in succession activates the LED array 16, etc.). The adapter 10 may also include a timing mechanism 34.

The timing mechanism 34 may be an oscillator, crystal, conventional clock, or the like. The timing mechanism 34 may control the operation of microprocessor 31 in accordance with the program from the memory 32. In addition, the timing mechanism 34 may be used to control the length of a presentation of light, and/or aroma set by a program in memory 32, as programmed by a user.

The intensity and exact color of the light emitted from the adapter 10 may be varied by changing the current applied to each diode. The different combinations of LED 14 operations will alter the perceived color when the light from the LEDs 14 is diffused to form one perceived color. This is best understood in connection with the exemplary CIE chart of FIG. 3 with three coordinates corresponding to three colored (red 14a, green 14b and blue 14c) LEDs. The colored light show as described herein includes starting and ending color points and proceeding along any predefined path between those two points during the course of a show.

A color point refers to the settings of the LEDs 14 at a given moment of the colored light show, which provides a specific perceived color. As the settings of the LED array 16 change over time in accordance with the instructions for the colored light show, the color points can ultimately be perceived as a "wash" or "waves" of colors. Because we are discussing "perceived" colors, the starting color point does not directly correspond to the wavelengths of light emitted by the LEDs 14 used in the color light show, inasmuch as those wavelengths are substantially constants. The starting and ending color points can, however, be defined by coordinates on the CIE chart of FIG. 3.

The color points can also be defined by the relative intensities of the lights emitted from the LEDs 14 used to produce the color light show (e.g., the operational settings for the different LEDs 14 at specified points of the colored light show). For instance, a color point can be defined by the specific intensity level set at that point in time for each LED 14 being used, and the dominant wavelength of each LED 14. Preferably, intensity levels will be defined by the pulse widths of the LEDs 14 (e.g., as a percentage of full intensity of the LEDs 14).

It will be understood by one of ordinary skill in the art that the combination of the lights from different-colored LEDs 14 at specified intensities will directly correspond to a set point on the CIE chart. Therefore, the different possible methods discussed above for defining the color points (e.g., using CIE chart coordinates or specific LED 14 settings) are substantially equivalent for purposes of defining a perceived color.

We note, however, that there are many ways in which the lights from the different LEDs 14 can be combined. In some methods, especially where diffusers 15, 15a are not used and the LEDs 14 are merely placed in close proximity to each other, a user may perceive different colors close to the emission points of the LEDs 14. When we discuss color points, we refer to the color of a substantially complete mixture of the lights from the different LEDs 14, even though there may be observable portions of the display in which the user sees distinct colors corresponding to the wavelengths from the individual LEDs 14, rather than the complete mixture.

The starting and ending color points are similar to the first and last entries in a look-up table setting forth all of the points of a color show in a conventional system; however, instead of providing all of the intervening points from the conventional look-up table, the adapter 10 can dispense with the need to determine and store each and every intervening color point. To achieve this effect, the above-referenced timing information is provided. The timing information defines timing aspects of the colored light show and LED 14 control.

Using the timing information, a microprocessor 31 may calculate all of the intervening color points for the colored light show on its own. This saves valuable memory space that would otherwise have to be devoted to complex look-up tables for various colored light shows. The timing information preferably includes information concerning the duration of the show, from display of the starting color point to the ending color point. The timing information also preferably includes information concerning the ramp speed for the LEDs 14, either as a whole, or individually. The ramp speed refers to the speed of intensity change of the LEDs 14. Generally, ramp speed may be defined as the unit of time it takes the LED 14 to change one intensity level (for that particular show), with each intensity level being equal. This can also be defined as the change of intensity per unit of time.

The LEDs 14 may be controlled by pulse width modulation (PWM) such that the pulse width of a constant current applied for a portion of the duty cycle is varied to alter the intensity of the light emitted from the LED 14. The intensity level of the LED 14 can be measured as a fraction of the duty cycle during which the constant current is applied, which, among other ways, can be expressed as a percentage. When an LED 14 is not on, the pulse width is at 0%. When a constant current is applied to the LED 14 for half of the duty cycle, the intensity of the LED is at 50%. Ramp speed may be defined as the amount of time between changes of intensity of one percentage point of total intensity. Consequently, if the ramp speed of an LED 14 is set at two seconds, then during the course of the colored light show that LED 14 will change its intensity by one percentage point every two seconds until reaching the target value (i.e., the intensity value of the LED 14 for achieving the ending color point). In an embodiment, ramp speed is defined as the percentage change per second. Of course, the speed can be defined in any one of a number of ways, as would be understood by one of ordinary skill in the art. Also, the ramp speed can be a positive or negative value, depending on whether the intensity of the LED 14 is to be increased or decreased during the colored light show. Alternatively, a microprocessor 31 can be programmed to increase or decrease the intensity setting by comparing the starting intensity setting to the ending intensity setting. Thus, for instance, if the microprocessor 99 determines that the value of the ending setting is lower than the value of the starting setting, the microprocessor 99 will decrease the intensity of the LED 14 at a rate set by the given ramp speed.

Figure 3:
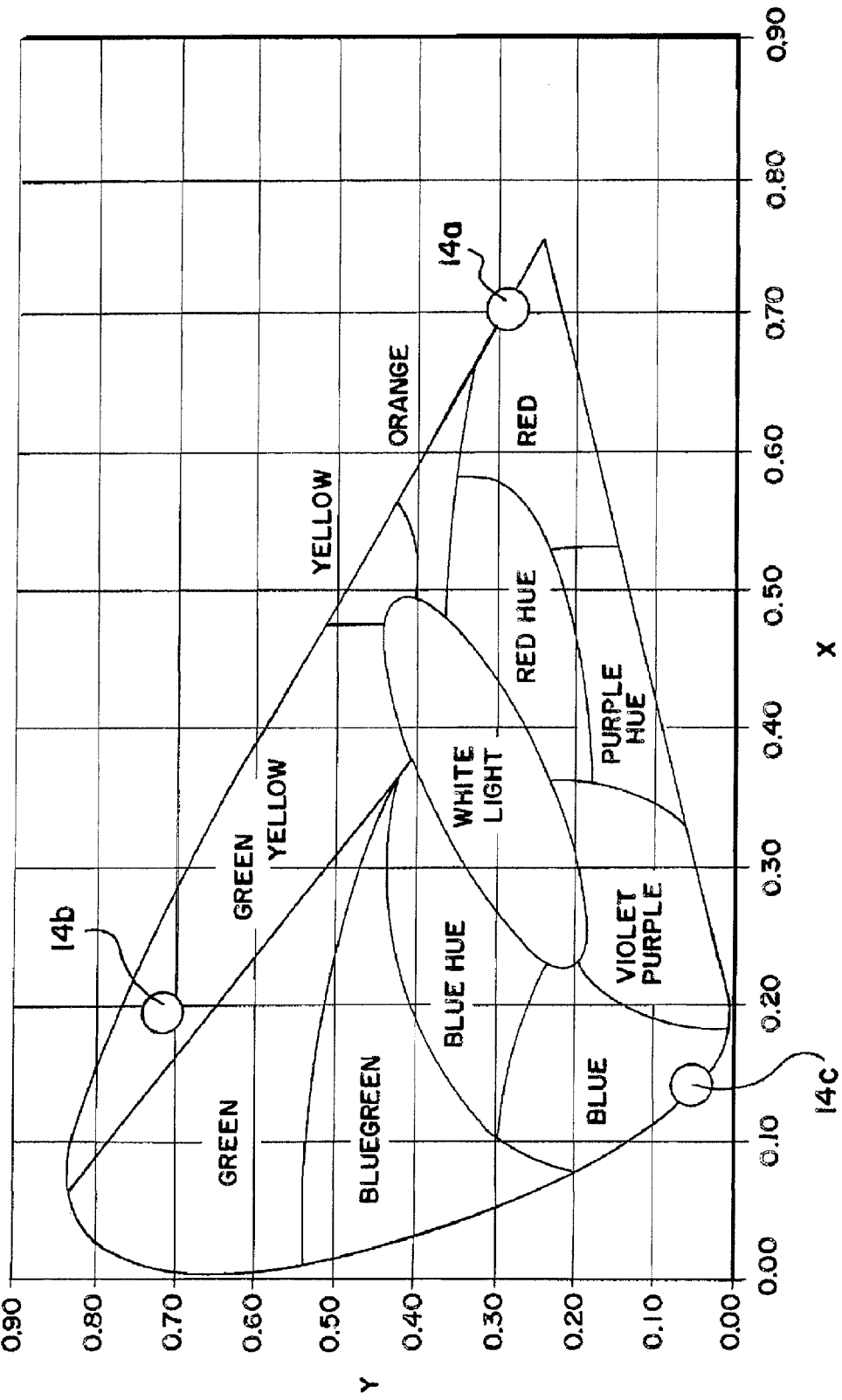
FIG. 3 shows an exemplary CIE chart with three coordinates corresponding to three LEDs of different colors, red, green and blue, wherein a colored light show presented in accordance with this disclosure comprises any path disposed within the boundaries of the curve carried out over time.

With the timing information provided, the microprocessor 31 controlling the LEDs 14 may be provided with logic that calculates the intervening color points between the starting and ending points of the CIE chart of FIG. 3. The logic reads the timing information from memory 32 and adjusts the duty cycle for each LED 14 in accordance with the ramp speed and target intensity. The intensity for each LED 14 is adjusted until the target value is reached or the duration of the show has been reached. At this time, the microprocessor 31 will read the next set of timing information from memory 32 and begin again. Of course, if the target intensity is reached prior to the duration of the show, the microprocessor 31 will hold the intensity of the LED 14 until the duration is reached. If a continuously changing show is desired, the ramp speed may be set such that the target intensity is not reached prior to the duration of the show and thus, the target value will never be reached. Likewise, the microprocessor 31 may be configured to ignore the duration, and load the next intensity and ramp speed as soon as the target intensity is reached.

The programming for achieving this would be readily understood by one of ordinary skill in the art. Accordingly, a detailed description of the many different ways of programming the microprocessor 31 will not be provided herein.

Control Mechanisms

As discussed above, the components for emitting light and an active may be configured to work in coordination with each other in any one of a number of ways. Provided below are preferred embodiments for configuring and controlling the various disclosed devices to emit light and fragrance. These are, however, only preferred embodiments, and numerous other configurations are possible.

Figure 7A:
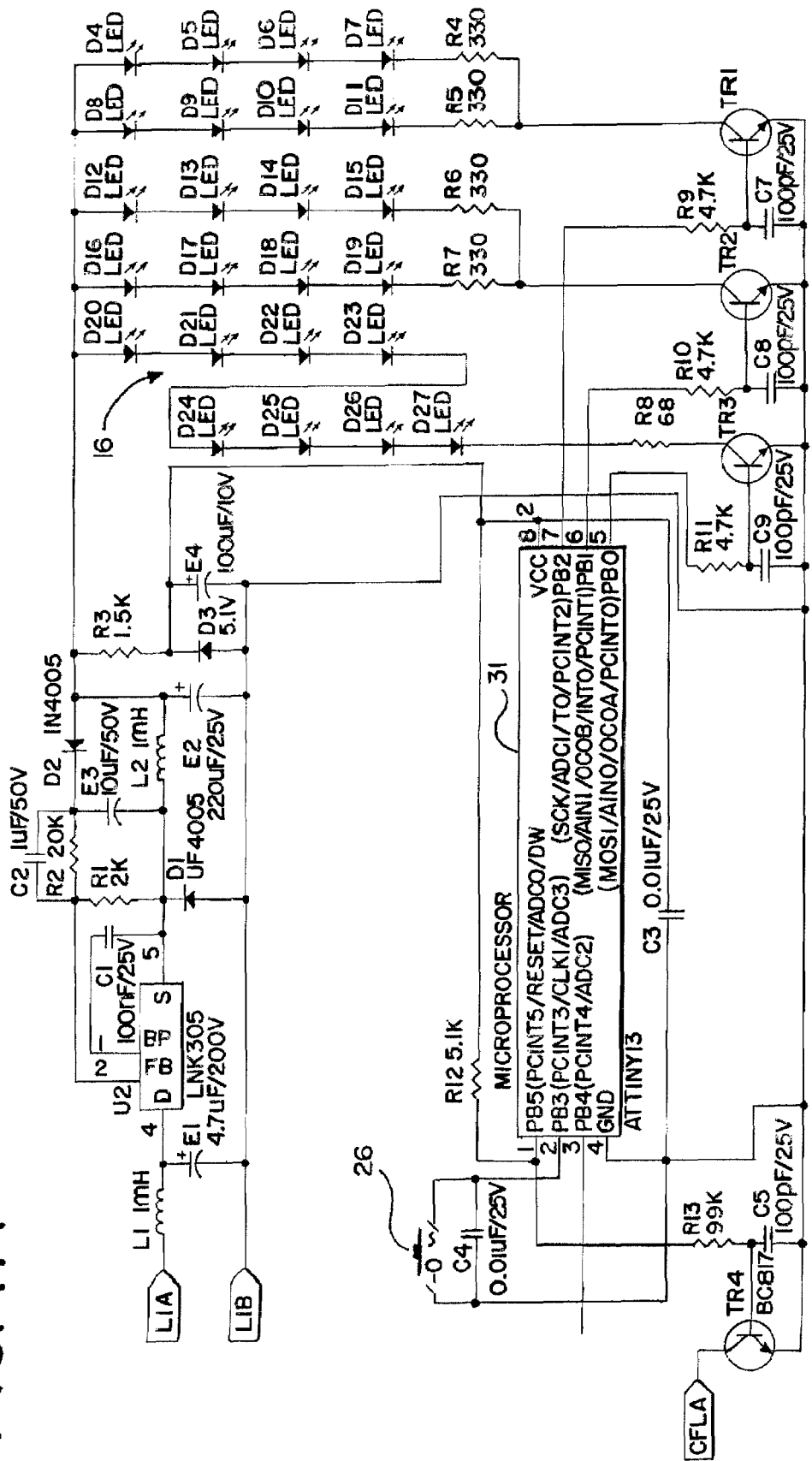
FIG. 7A is a circuit diagram of an exemplary LED driver circuit and corresponding LED array for the adapters shown herein.

Referring to an exemplary schematic as in FIG. 7A, the single switch 26 corresponds to a button or control switch 26 that, when first pushed, allows the LED driver to power up. The LED driver can be considered everything to the left of the LED array 16 which is shown in the upper right-hand corner of FIG. 7A. Subsequent pushing of the switch 26 allows the user to scroll through a preset program, such as the exemplary sequence of actions shown in the table of FIG. 7B.

In the sequence shown in FIG. 7B, there are three colored light shows. Subsequent pushing of the switch 26 allows the user to scroll through the three colored light shows, execute a sequence of the three colored light shows, power the unit off, return to the initial state and run a diagnostics program.

The LED driver is a constant current mode buck-boost converter, which bucks (lowers) or boosts (increases) the line voltage to match the required line voltage required to power the LED array 16. The LED array 16 may include any number of LEDs 14, although twenty-four, or eight RGB clusters, are shown in FIG. 7A.

Each group of series-connected LEDs 14 is isolated from the microprocessor 31 by a transistor TR1, TR2 or TR3 for selectively shunting around the group of LEDs 14 and protecting the microprocessor 31 from the higher operating voltage of the LEDs 14. Thus, the microprocessor 31 is not at the same or similar voltage as the LEDs 14. The groups of series-connected LEDs 14 can be connected in series to take advantage of the efficiency and other performance benefits of series connections, and at the same time, each group can be controlled individually. The series arrangement of the LEDs 14 allows all of the LEDs 14 to be activated by only the three transistors TR1, TR2 and TR3.

The series-connected arrangement of the LEDs 14 is driven by a relatively high voltage, low current load, which can be more economically driven than a comparable high current, low voltage load. Connecting the LEDs 14 in series as described above, creates a higher voltage drop than for a single LED, since the voltage drops of the series-connected LEDs 14 are cumulative. This high cumulative voltage drop allows for a more efficient power supply, since the supply voltage is closer to the line voltage. However, this relatively high voltage is much greater than that required by most conventional, low cost controllers, microprocessors, etc., which typically require approximately 3.3 V to 16 V. The most common microprocessors require approximately 3.3 V to 5 V.

The microprocessor 31 provides a control signal to control the transistors TR1, TR2 and TR3, which in turn control the LED array 16. For example, the microprocessor 31 can preferably activate various pre-programmed colored light shows stored in memory 32 (not shown in FIG. 7a, e.g., onboard, external, and/or removable memory) to change the activation and/or intensity of the LEDs 14 in the LED array 16, or to hold a particular color that is currently being generated by the LEDs 14.

When the LED driver is turned on, current flows through the inductor L1 and capacitor E1 to form a half-wave rectifier to provide a DC voltage across E1. The DC voltage across E1 drives a switching power supply that is operated in constant current power mode, comprising an integrated power metal oxide field effect transistor (MOSFET) in the control module U2, the inductor L2, diode D1, and the capacitors E3 and C2.

Control module U2 preferably comprises a high frequency switching buck-boost converter, such as part number LNK305 as shown. Control module U2 has 4 pins: feedback (FB), bypass (BP), drain (D), and source (S). The control module U2, inductor L2, diode D1, and capacitors C2 and E3 are configured in a buck-boost topology, to lower the line voltage to that needed to drive the LEDs 14. A current sense resistor R1 provides a sample of the load current back to the control module U2. This sampling sets the current provided by the power supply in constant current mode. In the exemplary circuit shown in FIG. 7A, the internal MOSFET of control module U2 conducts, or is turned on, when the BP pin voltage exceeds 4.85V and the input current delivered to the FB pin is less than 49 µA. If a current in excess of 49 µA is applied to the FB pin, the internal MOSFET does not conduct, or is held off. When the internal MOSFET of control module U2 is on, current is delivered to the LEDs 14 via inductor L2, diode D3, and freewheeling diode D2. When the internal MOSFET of control module U2 is off, stored energy in inductor L2 delivers power to the LEDs 14 via diode D3 and freewheeling diode D2.

Resistors R1 and R2, and capacitors C1 and C2 provide a feedback network to control the switching of the internal MOSFET of control module U2. Capacitor C2, which is in parallel with current sense resistor R2, averages the pulsing voltage across current sense resistor R2. The current sense resistor R1 is sized such that when the voltage across it reaches a predetermined level, the divider network created by resistors R2 applies a current greater than a predetermined amount to the FB pin of the control module U2, thereby turning the internal MOSFET of the control module U2 off. When the voltage across resistor R2 is less than a predetermined level, the current delivered to the FB pin is less than a predetermined level and the internal MOSFET of control module U2 is allowed to turn on.

The internal circuitry of the control module U2 is powered by a capacitor C1 when the internal MOSFET is on. When the internal MOSFET is off, C1 is charged. The capacitor C1 provides a small current from the internal MOSFET source voltage at the BP pin to activate the internal voltage supply of the control module U2. This allows the control module U2 to run continuously.

Microprocessor 99 is programmed such that, when powered, it outputs three PWM signals at pins 5, 6 and 7. The PWM signals are coupled directly to the transistors TR1, TR2 and TR3. When pins 5, 6 and/or 7 of the microprocessor 99 provide a logical high (5 V) signal to one of transistors TR1, TR2 or TR3, the corresponding transistor opens, or is turned off. When pins 5, 6 and/or 7 of the microprocessor 99 provide a logical low (0 V) signal to the one of transistors TR1, TR2 or TR3, the corresponding transistor closes, or is turned on. When the transistors TR1, TR2 and TR3 are off (open), current flows normally from the buck-boost converter through the LEDs 14. When the transistors TR1, TR2 and TR3 are on (closed), current is diverted away from the LEDs 14 and is shunted around the LEDs 14 associated with each closed transistor TR1, TR2 and/or TR3. Since there is independent control of each transistor TR1, TR2 and TR3, current can be diverted away from each individual group of LEDs 14. In this way, the microprocessor 99 can use PWM to control current to each group of LEDs 14 individually.

The average current applied to each group of LEDs 14 can also be adjusted by changing the duty cycle of the PWM signal applied to that group through the opening and closing of the transistors TR1, TR2 and TR3. Thus, by adjusting the duty cycle applied to each transistor TR1, TR2 and TR3, the average current applied to each group of LEDs 14 per cycle can be adjusted, and hence the brightness/intensity of each group can be adjusted. The control mechanism may further include a dimming circuit for adjusting the brightness of the illumination source connected to the female socket 27, 27b.

Controlling the relative intensities of the red 14a, green 14b, and blue 14c LEDs in proximity on a printed circuit board using PWM current control allows for the generation of over 256 different perceived colors. Preferably, the PWM signal is at a frequency high enough that there is no noticeable flicker, and so that the human eye perceives only a blended color based upon the proportion of red 14a, green 14b, and blue 14c light emitted from the LED 14 groups. Alternatively, the frequency can be lowered, so that perceivable flickers or flashes of the light emitted are observable.

A capacitor E4 connected between the output of the switching power supply and the power return helps to stabilize the switching power supply by providing load current smoothing, such that the current supplied to the LEDs 14 is approximately DC with a small amount of AC ripple. Capacitor E4 provides a modest amount of filtering for the power supply. Additional capacitance is distributed among capacitors C7, C8 and C9, which are arranged in parallel with the transistors TR1, TR2 and TR3. The distributed capacitance arrangement suppresses the LED pulse currents delivered by capacitor E4 when any of the transistors TR1, TR2 or TR3 close. The three capacitors C7, C8 and C9 are effectively in series such that the reciprocal capacitances are cumulative (preferably about 3.3 µF each, for a cumulative equivalent of 1.1 µF). However, because each of the capacitors C7, C8 and C9 is in parallel with the respective group of LEDs 14, the capacitors no longer provide a source of surge current to its respective LED string. This is because the capacitors are always at the potential of the respective LED string. In this manner, a high value of capacitance can be obtained for stabilizing the switching power supply, while avoiding the surge current and the associated light flashes that occur when a large capacitance is connected in series with the groups of LEDs 14.

The microprocessor 31 may monitor the temperature delivered to the active insert 22 through the use of a temperature sensor. In this case, the microprocessor 31 can adjust the current through the heating resistor 18 to keep a constant temperature to the active insert 22 regardless of the orientation of the bulb or fixture used. Thus, the proper amount of heat is provided to the insert 22, regardless of the type of white light source (for example, incandescent, fluorescent, coiled fluorescent or white LED) or the orientation of the white light source. The sensor provides feedback to the microprocessor 31 so the correct temperature of the insert 22 is maintained. Different fragrances and different actives such as different insecticides or insect repellents will require different temperatures for proper emission rates.

Additionally, the temperature sensor 35 and microprocessor 31 may adjust the heat to deliver more fragrance or active at one point in a particular colored light show and less fragrance or active at a different point or time in a particular colored light show to enhance the user experience. For example, certain color schemes of the colored light show may require more or less fragrance or active than other color schemes of a colored light show. By way of one example that is not intended to be limiting, it may be beneficial to emit more fragrance during a blue/green portion of the colored light show and less fragrance during a red/orange portion of the same colored light show. Other active emission rates can be controlled according to a colored light show or according to other outside sources.

Further, in the case where a memory card is disposed on the active insert 22, the memory card may contain temperature information that is communicated to the microprocessor 31 that, in turn, is used to set the optimum temperature for that active optimize release of the active.

The microprocessor 31 may also be configured to send a varied control signal to the volatile active dispenser 17. More specifically, the current passing through a heater resistor 18 may be varied by the microprocessor 31. In such embodiments, the microprocessor 31 may vary the current to the resistor 18 according to user inputs (control switches 26 or buttons), or an automation device. Typically, the resistor 18 is placed adjacent to an area at which a volatile active ingredient is exposed to air and the heat from the resistor 18 causes the volatile active to be vaporized. In alternative embodiments, the resistor 18 may be replaced and/or supplemented by a fan which is controlled by a switch 26, or an atomization device. Further, the volatile active dispenser may also be mechanically adjusted by a user, rather than through a microprocessor.

Microprocessor 31 may also control a refill cue. The refill cue tracks the use of volatile active control to estimate the time at which the volatile active in the volatile active dispenser is likely to be used up. When the refill cue determines that volatile active has been spent, it sends a signal to the LEDs 14 to illuminate in a pattern, color, or other manner to indicate to a user that it is time to replace the volatile active in the dispenser 17 if a refillable dispenser is used, or more preferably, the volatile active inserts 22 shown in FIGS. 1A and 2A-2D. A large variety of cartridge-type containers or inserts 22 may be utilized for the "inserts" 22 disclosed herein. Various other designs will be apparent to those skilled in the art. Further, suitable means for determining or communicating to the refill cue when a particular insert 22 is empty or near-empty will also be apparent to those skilled in the art. A simple resistance mechanism may be desirable due to low-cost and dependability.

In a preferred embodiment, the fluorescent lamp or CFL is equivalent to a 60 W incandescent light bulb. Typically, it takes two minutes to reach 60 W. The refill cue function may either be a timer device, such as a 30 day timer, or may include a sensor to determine whether an insert is actually depleted. In any event, a sound function may be incorporated into the refill cue.

Figure 8A:
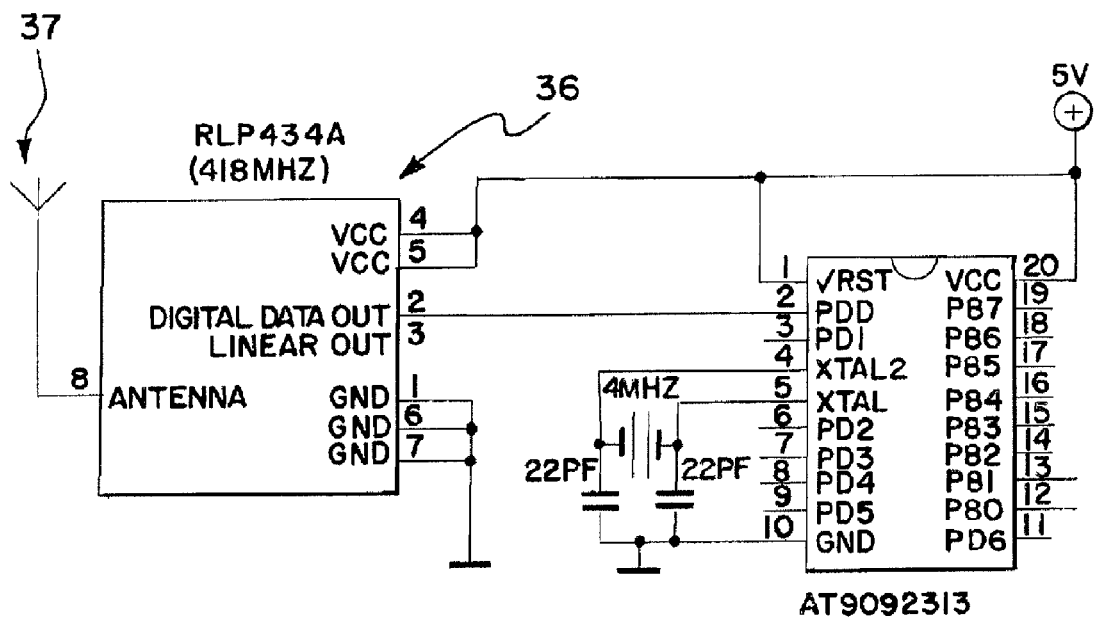
FIG. 8A is a circuit diagram for the radiofrequency (RF) receiver for adapters employing a remote control.
Figure 8B:
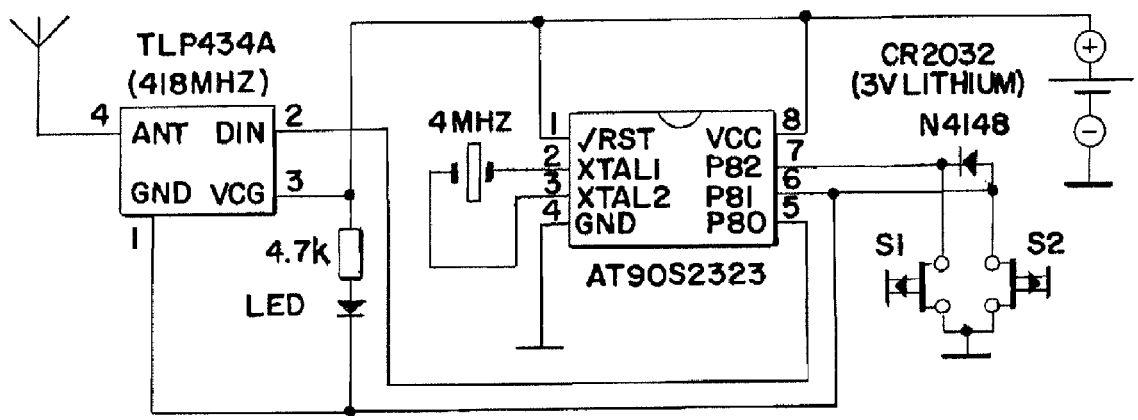
FIG. 8B is a circuit diagram for the RF transmitter for adapters employing a remote control.

The control mechanism may be programmed/controlled in any number of ways. In one embodiment, a radio-frequency (RF) transceiver 36 receives an external signal, through an antenna 37, from a remote control, as represented by circuits in FIGS. 8A-8B. That signal is transmitted from the RF transceiver 36 to the microprocessor 31 to set the presentation of light through an LED driver and the volatile active dispenser 20. Also, the operation of the control mechanism may be set by an internal program.

A user may manually set the volatile active output and colored light show. In this case, a program select control switch 26 (FIG. 5) may be operated by a user to set a colored light show program for the LEDs 14.

Of course, additional buttons or control switches 26 may be provided, depending on the level of the control and programmability desired. In particular, an added switch 26 can be provided to control whether manual or automatic operation/programming is desired. Further, switch mechanisms may be in the form of a single switch, a toggle switch, a lanyard-type switch, one, two and three button type interfaces, rotating switches or dials built into the adapter and remote controls.

Additional colored light shows may be supplied by way of memory cards or chips either separate from or in connection with the replacement fragrance or active inserts 22. Thus, the consumer can conveniently and inexpensively match the fragrance or volatile active with a colored light show or light theme. The refills or inserts 22 may be directly connected to the controller or device conducting the colored light show or communication between the memory chip or memory card and the controller can be accomplished through radio frequency identification (RFID) technology as disclosed above in FIGS. 8A-8B. Fragrance or active vapor delivery may be constant for each mode or may be varied as heater boost settings may be incorporated into the switch mechanisms for the devices that include a heating element, such as heater resistor 18. The heating elements can be designed to mimic the heat generated by a fluorescent bulb (140° F.) to keep a constant delivery of fragrance when the device is used for conventional white light or when the device is used for displaying a colored light show.

Preferably, the memory 32 will store data concerning the colored light show, as discussed above. This data may include starting color points, ending color points, duration information for segments/shows, ramps speeds, other timing information, and the like. The microprocessor 31 may have onboard program memory or external program memory containing the instructions for interpreting the colored light show data, calculating intervening light points, and controlling the LEDs 14 based at least in part on the color data and timing information. Thus structured, memory 32 storing the colored light shows does not need the full range of data typically provided in look-up tables used to define colored light shows.

The size of the external memory and extent of the program stored therein to instruct the microprocessor 31, and the extent of the program stored onboard the microprocessor 31 in the manufacturing process can be determined based on design needs. Also, in future replacement memory cards, where such are used, additional logic can be provided to control the microprocessor 31, when additional information is needed to operate the new colored light shows. One of ordinary skill in the art would appreciate the different ways of dividing up such information between the memory 32 and microprocessor 31. However, in a preferred embodiment, the system is defined such that microprocessor 31 contains the operating instructions for the colored light shows and the memory 32 contains the operating instructions for the colored light shows and thus the timing, intensity and ramp speed data for each LED 14 used in the colored light shows.

The embodiments described above adapt to receive conventional incandescent light bulbs and can be received in a conventional light socket. Not only can the disclosed devices be used in conventional lamp fixtures and light sockets, the disclosed devices can be useful in closets and used for outdoor lighting purposes as described above. When used outdoors, one suitable combination is colored and white light emission with insect control.

All the devices include fragrance or active ingredient refills or inserts 22 so the user can switch fragrances or active ingredients and coordinate such fragrances with the colored light show of the device. Alternatively, the colored light shows or colored light themes may be coordinated with the volatile active emissions. Moreover, the colored light shows or colored light can be used to set the mood when the volatile active is an aromatherapy material, a medicine or medicinal fragrance.

The figures show only possible arrangements for configuring and controlling the disclosed devices. Many different embodiments may be constructed without departing from the spirit and scope of our invention. It should be understood that disclosure is not limited to the specific embodiments described in this specification. To the contrary, this disclosure is intended to cover various modifications and equivalent arrangements included within the spirit and scope of this disclosure as defined by the claims. The scope of the claims is to be accorded the broadest interpretation so as to encompass all such modifications, equivalent structures and functions.

INDUSTRAIL APPLICABILITY

The devices of this disclosure make it possible to achieve an overall desired effect by providing mood lighting, active ingredient emission, and a functional light source from a single adapter which mates with a conventional lamp or light socket.

While only certain embodiments have been set forth, alternatives and modifications will be apparent from the above description to those skilled in the art. These and other alternatives are considered equivalents and within the spirit and scope of this disclosure and the appended claims.

What is claimed:

1. A combination light source and controlled volatile active dispenser adapter, comprising:
    a base comprising a male connector for engaging a light socket and a female socket for receiving an illumination source,
    the base further comprising an active dispenser comprising a slot for receiving a replaceable insert,
    the base being connected to an annular diffuser through which the illumination source is received before it engages the female socket, and
    the base supporting at least one light emitting diode (LED) positioned beneath the diffuser and a control circuitry for controlling the illumination source and the at least one LED, wherein the control circuitry comprises a memory with at least one colored light show stored in the memory, and a colored light show is selected from a plurality of colored light shows based on the replaceable insert received in the slot of the active dispenser.

2. The adapter of claim 1, wherein the at least one LED comprises at least one red, green and blue (RGB) LED cluster.

3. The adapter of claim 1, wherein the control circuitry comprises a heater circuit for heating the replaceable insert.

4. The adapter of claim 1, wherein the control circuitry comprises a dimmer circuit to adjust a brightness of the illumination source.

5. The adapter of claim 1, wherein the control circuitry controls an output rate from the active dispenser.

6. The adapter of claim 1, wherein the control circuitry comprises a refill cue that provides an indication when the replaceable insert has been depleted.

7. The adapter of claim 1, wherein the replaceable insert comprises a memory with at least one colored light show stored in the memory.

8. The adapter of claim 1, wherein the illumination source comprises at least one low voltage light source.

9. The adapter of claim 1 further comprising at least one control switch.

10. The adapter of claim 1 further comprising a remote control having a transmitter and a corresponding receiver within the control circuitry.

11. The adapter of claim 1, wherein the active in the replaceable insert is selected from the group consisting of a fragrance, an air sanitizer, an air deodorizer, an insecticide, an insect repellant, an insect attractant, a medicine, an aromatherapy oil, and combinations thereof.

12. A combination light source and controlled volatile active dispenser adapter, comprising:
    a base comprising a male connector for engaging a light socket and a female socket for receiving an illumination source,
    the base further comprising an active dispenser comprising a slot for receiving a replaceable insert,
    the base being connected to an annular diffuser through which the illumination source is received before it engages the female socket,
    the base supporting at least one RGB LED cluster positioned beneath the diffuser, and a control circuitry comprising a memory and a heater circuit;
    wherein the control circuitry comprises a memory with a plurality of colored light shows stored in the memory, and the colored light show is selected from the plurality of colored light shows based on the replaceable insert that is received in the slot.

13. The adapter of claim 12, wherein the control circuitry comprises a dimmer circuit to adjust a brightness of the illumination source.

14. The adapter of claim 12, wherein the control circuitry controls an output rate of the active dispenser.

15. The adapter of claim 12, wherein the control circuitry comprises a refill cue that provides an indication when the replaceable insert has been depleted.

16. The adapter of claim 12, wherein the replaceable insert comprises a memory with at least one colored light show stored in the memory.

17. The adapter of claim 12, wherein the illumination source comprises at least one low voltage light source.

18. The adapter of claim 12 further comprising at least one control switch.

19. The adapter of claim 12 further comprising a remote control having a transmitter and a corresponding receiver within the control circuitry.

20. The adapter of claim 12, wherein the active in the replaceable insert is selected from the group consisting of a fragrance, an air sanitizer, an air deodorizer, an insecticide, an insect repellant, an insect attractant, a medicine, an aromatherapy oil, and combinations thereof.

21. A combination light source and controlled volatile active dispenser adapter comprising:
   a male connector for engaging a light socket;
   a female socket for receiving an illumination source;
   a slot for receiving a replaceable insert;
   an annular diffuser through which the illumination source is received before engaging the female socket;
   at least one RGB LED cluster; and
   a control circuitry comprising memory for storing a plurality of colored light shows and circuitry for controlling an intensity of the illumination source;
   wherein the control circuitry comprises a memory with at least one colored light show stored in the memory;
   wherein the colored light show is selected from a plurality of colored light shows based on the replaceable insert received in the slot of the active dispenser
   and at least one switch performing one or more functions selected from the group consisting of
   activating a colored light show and turning off the illumination source, turning on the illumination source and deactivating the colored light show, turning off both the illumination source and colored light show; freezing the colored light show; adjusting an intensity of the illumination source; adjusting an intensity of one or more of the LEDs; adjusting an output rate from the replaceable insert; and scrolling through the plurality of colored light shows stored in the memory.

* * * * *